United States Patent [19]

Moedritzer

[11] 4,101,587
[45] Jul. 18, 1978

[54] METHOD FOR THE MANUFACTURE OF ORGANO SUBSTITUTED PHOSPHONIUM SALTS

[75] Inventor: Kurt Moedritzer, Webster Groves, Mo.

[73] Assignee: Monsanto Company, St. Louis, Mo.

[21] Appl. No.: 640,380

[22] Filed: Dec. 15, 1975

[51] Int. Cl.$^2$ ............................................. C07F 9/54
[52] U.S. Cl. ............................................. 260/606.5 F
[58] Field of Search ................................. 260/606.5 F

[56] References Cited

U.S. PATENT DOCUMENTS

| | | |
|---|---|---|
| 2,743,299 | 4/1956 | Flynn ........................... 260/606.5 F |
| 2,912,466 | 11/1959 | Reuter ......................... 260/606.5 F |
| 3,007,969 | 11/1961 | Reüter et al. ................. 260/606.5 F |
| 3,013,085 | 12/1961 | Buckler ........................ 260/606.5 F |
| 3,243,450 | 3/1966 | Grayson .................... 260/606.5 F X |
| 3,666,817 | 5/1972 | Carlson ........................ 206/606.5 F |
| 3,755,457 | 8/1973 | Carlson ........................ 260/606.5 F |

OTHER PUBLICATIONS

Reeves et al., J.A.C.S. 77, pp. 3923–3924, (1955).

*Primary Examiner*—Helen M. S. Sneed
*Attorney, Agent, or Firm*—Herman O. Bauermeister; John D. Upham

[57] ABSTRACT

Substituted phosphonium salts such as tetrakis(hydroxymethyl)phosphonium chloride are prepared by reacting a metal phosphide selected from the group consisting of lithium phosphide, sodium phosphide, potassium phosphide, beryllium phosphide, magnesium phosphide, calcium phosphide, strontium phosphide, barium phosphide, boron phosphide, aluminum phosphide, gallium phosphide, and zinc phosphide, with an aldehyde having from 1 to 12 carbon atoms, the proportion of the aldehyde being at least 4 moles per gram atom of the phosphorus in the said phosphide. The reaction is conducted with at least one and a half moles of water per gram atom of phosphorus in the said phosphide and at least one mole of mineral acid being present per gram atom of phosphorus in the said phosphide, with or without a catalyst, and in the presence of an inert gas atmosphere. The products are fire retardants.

9 Claims, No Drawings

METHOD FOR THE MANUFACTURE OF ORGANO SUBSTITUTED PHOSPHONIUM SALTS

BACKGROUND OF THE INVENTION

The present invention relates to a process for the preparation of substituted phosphonium salts such as tetrakis(hydroxymethyl)phosphonium chloride. More particularly the present invention is directed to a new method for the preparation of such compounds which avoids the difficulties of prior art processes such as the necessity for employing highly toxic and difficult to handle reactants, such as phosphine, as starting materials.

Other prior art processes for the production of phosphonium salts have employed phosphine, $PH_3$, as the starting material, but this compound is dangerous and difficult to work with. Phosphine is a gas which ignites spontaneously when mixed with air, so that rigid safety precautions are necessary in employing phosphine in an industrial organic preparation.

SUMMARY OF THE INVENTION

The present invention relates to a process for the preparation of substituted phosphonium salts such as tetrakis(hydroxymethyl)phosphonium chloride. More particularly the present invention is directed to a new method for the preparation of phosphonium salts which avoids the difficulties of prior art processes such as the necessity for employing highly toxic reactants, for example phosphine as the starting material.

Essentially the process yields the compound $P[CH(OH)R]_4X$ in which the R is H or an alkyl, alkylaryl or aromatic radical of from 1 to 11 carbon atoms, by reacting a metal phosphide selected from the group consisting of lithium phosphide, sodium phosphide, potassium phosphide, beryllium phosphide, magnesium phosphide, calcium phosphide, strontium phosphide, barium phosphide, boron phosphide, aluminum phosphide, gallium phosphide and zinc phosphide, with at least 4 moles, or preferably from 4 to 10 moles of an aldehyde having the formula RCHO, per gram atom of phosphorus, and at least 1, or preferably from 1 to 10 moles of a mineral acid, per gram atom of the phosphorus of the said phosphide. The reaction is conducted at a temperature of from $-10°$ C to $100°$ C, or preferably $0°$ C to $50°$ C, and still more preferably $0°$ C to $25°$ C, in the presence of an inert gas atmosphere, and with at least one and a half moles of water being present per gram atom of phosphorus of the said metal phosphide. A preferred range of the water proportion is from 1.5 to 30 moles, and a more preferred range is from 1.5 to 10 moles.

It has now been found that substituted phosphonium salts such as tetrakis(hydroxymethyl)phosphonium chloride may be readily prepared utilizing a metal phosphide of the aforesaid group. A preferred group is magnesium phosphide, calcium phosphide, aluminum phosphide, and zinc phosphide as the starting material to provide a reactive source of phosphorus. The phosphides employed in the present invention are stable and safe materials, easy to work with, and readily available on the commercial market, or prepared from the corresponding metal e.g. aluminum or zinc reacted with elemental phosphorus, with the metal phosphide being provided in particulate form, e.g. particles of 0.01 to 10 mm diameter. The aforesaid metal phosphides are also surprisingly active.

In particular, the present invention, making use of metallic phosphides as the phosphorus source, avoids the necessity for the use of phosphine. In the process of the invention, the metal phosphide undergoes reaction at the surface thereof to form the desired products, so that the evolution of phosphine is avoided. The mechanism of the present reaction apparently proceeds without the formation of phosphine. The reaction may thus be conducted with simple low-pressure equipment. Gaseous phosphine, which is well-known to ignite spontaneously when it is mixed with air, is not evolved from the reaction mixture.

DESCRIPTION F THE PREFERRED EMBODIMENTS

Organic reactants which are employed in the present invention for the preparation of phosphonium salts are aldehydes having 1 to 12 carbon atoms. Preferred aldehydes are the alkyl and alkylaryl compounds of 1 to 12 carbon atoms, and also having substituents such as —CN, —Br and —Cl groups optionally present.

The general formula for the aldehyde starting material is RCHO, where R is an alkyl, alkylaryl, or aromatic group of 1 to 11 carbon atoms. Examples of such organic starting materials for the present process include phenylacetaldehyde, formaldehyde, acetaldehyde, propanal, butanal, pentanal, hexanal, heptanal, and decanal. Aromatic aldehydes such as benzaldehyde and tolualdehyde may also be employed. The products obtained when using aromatic aldehydes as starting material undergo rearrangement.

The aldehydes are employed in the proportion of at least 4 or preferably 4 to 10 moles per gram atom of the phosphorus of the metal phosphide. However, an excess of the aldehyde may be employed as a solvent, for example, 20 moles of acetaldehyde per gram atom of phosphorus.

The general chemical reaction exemplified by the use of aluminum phosphide with formaldehyde as the aldehyde is shown below. Hydrobromic acid is here shown as a representative acid, preferably used in excess, forming the bromide salt.

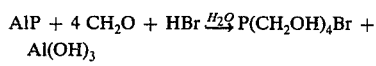

$$AlP + 4 CH_2O + HBr \xrightarrow{H_2O} P(CH_2OH)_4Br + Al(OH)_3$$

The products of the reaction are separated by conventional means such as filtration from the inorganic residue, or by solvent extraction. An advantage of the present process is that insoluble hydroxides of certain metals are formed; substantially the only soluble organic product is a good yield of the phosphonium salt.

The present reaction for the production of organo-substituted phosphonium salts with the aforesaid ratios of reactants avoids the formation of unstable compounds such as tetra(hydroxymethyl)phosphonium hydroxide which would decompose to phosphine oxides.

Other acids which may be employed to produce the present phosphonium salts include the mineral acids, generally, for example, phosphoric acid, nitric acid, sulfuric acid, hydrochloric acid, and hydriodic acid as well as hydrobromic acid. The proportion of acid is at least 1 mole of acid, and preferably from 1 to 10 moles per gram atom of phosphorus of the metal phosphide. It is desirable to have at least one mole of acid present to form the organo phosphonium salts, which are soluble, and easy to separate.

A catalyst is optional in the present process. The compounds of Group VIII metals, e.g. iron, cobalt, nickel, ruthenium, rhodium, palladium, osmium, iridium and platinum employed as salts, and complexes, e.g. chlorides, bromides, iodides, sulfates, phosphates or nitrates, for example iron chloride, cobalt bromide, nickel cyanide, as well as sodium chloroplatinate accelerate the reaction but are not essential. The proportion of catalyst is not critical, and may vary broadly, such as from 0.01 to 1% by weight of the reaction mixture.

The pressure imposed on the system is not a critical factor and may vary from vacuum conditions to atmospheric and superatmospheric pressures, e.g. 10 atmospheres. Because of the oxygen sensitivity of the reaction it is essential to use an inert gas atmosphere or stream such as hydrogen, nitrogen, argon or carbon dioxide in the reactor to prevent oxidation.

A solvent is also optional in conducting the reaction in order to provide better mixing of the organic component with the particulate metal phosphide. Examples of solvents which are inert include acetonitrile, benzonitrile, dioxane, tetrahydrofuran and other water soluble organic solvents. Proportions of the solvent are not critical, e.g. from 1 to 10 moles per mole of the aldehyde starting material. If desired an excess of the aldehyde reactant may also be used as a solvent.

The following examples illustrate specific embodiments of the invention but are not limitative of the scope of the invention.

EXAMPLE 1

The preparation of organo substituted phosphonium salts based upon the use of formaldehyde is conducted in a three-necked reaction vessel provided with a magnetic stirrer, a reflux condenser and feeding means for aluminum phosphide. The reactor is initially charged with 170 grams of concentrated hydrochloric acid (1.7 moles HCl and 5.95 moles $H_2O$), 171 grams of 37.1% formaldehyde (2.1 moles formaldehyde and 6 moles water) and as a catalyst 0.5 grams sodium chloroplatinate.

The reactor is also supplied with a nitrogen stream to prevent exposure of the reaction mixture to the atmosphere. The vessel is maintained at a temperature below 40° C, during the addition of ½ mole of finely divided (about 0.1 mm diameter) aluminum phosphide (29 grams) over a period of 2 hours with continued stirring. Agitation of the reaction mixture is conducted for 4 hours after which the vessel is cooled to room temperature. It is apparent that the reaction takes place on the surface of the metal phosphide particles so that there is no evolution of phosphine, nor is phosphoric acid formed.

The dark brown reaction solution is evaporated over a steam bath and later subjected to a vacuum. The product is extracted with 2-propanol.

In order to purify the product, the crude material is recrystallized from 2-propanol. From this solution the white crystalline solid product is obtained, tetrakis(hydroxymethyl)phosphonium chloride, $P(CH_2OH)_4Cl$, melting point 151°-152° C (literature value, 151° C.)

The reaction also leads to the same product when no catalyst is employed.

EXAMPLE 2

The phosphonium salts of the present invention are all useful as fire retardant additives, for example with cotton. For this purpose an add-on of 5-10%, for instance 10%, by weight relative to the cotton is applied from an aqueous solution, e.g. the tetrakis(hydroxymethyl)phosphonium chloride. This treatment improves the fire-retardancy of the cotton. In order to obtain a wash-resistant product, the treated cotton is subjected to ammonia(or an amine such as methylamine), and water washing treatments.

EXAMPLE 3

The preparation of tetrakis(hydroxyethyl)phosphonium iodide based upon the use of acetaldehyde is conducted in a three-necked reaction vessel provided with a magnetic stirrer, a reflux condenser and feeding means for sodium phosphide. The reactor is initially charged with 4 moles of concentrated hydriodic acid, 4 moles acetaldehyde and 6 moles water, and as a catalyst 0.5 grams nickel iodide.

The reactor is also supplied with an inert gas stream of nitrogen to prevent exposure of the reaction mixture to the atmosphere. The vessel is maintained at a temperature below 40° C during the addition of ½ mole of finely divided (about 0.1 mm diameter) sodium phosphide over a period of 2 hours with continued stirring. Agitation of the reaction mixture is conducted for 4 hours after which the vessel is cooled to room temperature, and the product separated from the reaction mixture.

EXAMPLE 4

The preparation of tetrakis(hydroxybutyl)phosphonium bromide based upon the use of butyraldehyde is conducted in a three-necked reaction vessel provided with a magnetic stirrer, a reflux condenser and feeding means for zinc phosphide. The reactor is initially charged with 2 moles of concentrated hydrobromic acid, 6 moles $H_2O$, 4 moles butyraldehyde and as a catalyst 0.5 grams rhodium chloride.

The reactor is also supplied with an argon stream to prevent exposure of the reaction mixture to the atmosphere. The vessel is maintained at a temperature below 45° C, with the addition of ½ mole of finely divided (about 0.1 mm diameter) zinc phosphide over a period of 2 hours with continued stirring. Agitation of the reaction mixture is conducted for 4 hours after which the vessel is cooled to room temperature, and the bromide salt product separated from the reaction mixture.

EXAMPLE 5

With heptaldehyde as the organic starting material the production of tetrakis(hydroxyheptyl)phosphonium chloride is conducted in a three-necked reaction vessel provided with a magnetic stirrer, a reflux condenser and feeding means for aluminum phosphide. The reactor is initially charged with 150 grams of concentrated hydrochloric acid (1.5 moles HCl and 5 moles $H_2O$), 100 grams (0.875 mole) of heptaldehyde and 2.1 moles of tetrahydrofuran as a solvent. No catalyst is used.

The reactor is also supplied with a nitrogen stream to prevent exposure of the reactants and products to the atmosphere. The vessel is maintained at a temperature below 40° C, with the addition of 0.21 moles of finely divided (about 0.1 mm diameter) aluminum phosphide (12.2 grams) over a period of 2 hours with continued stirring. Agitation of the reaction mixture is conducted for 4 hours after which the vessel is cooled to room temperature. The reaction takes place on the surface of the metal phosphide particles so that there is no evolution of phosphine, nor is phosphoric acid formed.

The dark brown reaction solution is evaporated over a steam bath and later subjected to a vacuum, and the chloride salt product separated.

EXAMPLE 6

With phenylacetaldehyde as the organic starting material the production of tetrakis[hydroxy(phenylethyl)]-phosphonium chloride is conducted in a three-necked reaction vessel provided with a magnetic stirrer, a reflux condenser and feeding means for aluminum phosphide. The reactor is initially charged with 150 grams of concentrated hydrochloric acid (1.5 moles HCl and 5 moles $H_2O$, 0.875 moles of phenylacetaldehyde and 2.1 moles of tetrahydrofuran as a solvent. No catalyst is used.

The reactor is also supplied with a nitrogen stream to prevent exposure of the products to the atmosphere. The vessel is maintained at a temperature below 40° C, with the addition of 0.21 mole of finely divided (about 0.1 mm diameter) aluminum phosphide (12.2 grams) over a period of 2 hours with continued stirring. Agitation of the reaction mixture is conducted for 4 hours after which the vessel is cooled to room temperature. The reaction takes place on the surface of the metal phosphide particles so that there is no evolution of phosphine, nor is phosphoric acid formed.

The dark brown reaction solution is evaported over a steam bath and later subjected to a vacuum, and the chloride product separated.

EXAMPLE 7

When the procedure of Example 1 is modified by a molar ratio of formaldehyde to the phosphorus (sodium phosphide in this example), at 6:1, or 8:1, or 10:1 the sole product remains tetrakis(hydroxymethyl)phosphonium chloride.

EXAMPLE 8

When the aluminum phosphide of Example 1 is substituted by equivalent proportions of lithium phosphide, sodium phosphide, potassium phosphide, beryllium phosphide, magnesium phosphide, calcium phosphide, strontium phosphide, barium phosphide, boron phosphide, gallium phosphide, or zinc phosphide, the reaction proceeds to the same product as in Example 1.

EXAMPLE 9

The use of other Group VIII metal compound catalysts is also effective in the procedure of Example 1. Equivalent proportions of ferrous chloride, iridium bromide, cobalt iodide and ferric nitrate yield similar products to those of Example 1. Other mineral acids, e.g. sulfuric, nitric or phosphoric acids used at equivalent proportions lead to the corresponding salts.

What is claimed is:

1. A process for preparing the compound $P[(CH(OH)R]_4X$ in which R is H or an alkyl or alkylaryl group of from 1 to 11 carbon atoms, and X is the anion of a mineral acid, HX, which comprises reacting a metal phosphide selected from the group consisting of lithium phosphide, sodium phosphide, potassium phosphide, beryllium phosphide, magnesium phosphide, calcium phosphide, strontium phosphide, barium phosphide, boron phosphide, aluminum phosphide, gallium phosphide, and zinc phosphide, with at least 4 moles of an aldehyde having the formula RCHO, per gram atom of the phosphorus, and at least 1 mole of the said mineral acid, per gram atom of the phosphorus, at a temperature of from $-10°$ C to $100°$ C in the presence of an inert gas atmosphere, and with at least one and a half moles of water being present per gram atom of the phosphorus of the said metal phosphide.

2. A process for preparing the compound $P[CH(OH)R]_4X$ in which R is H or an alkyl or alkylaryl group of from 1 to 11 carbon atoms, and X is the anion of a mineral acid, HX, which comprises reacting a metal phosphide selected from the group consisting of lithium phosphide, sodium phosphide, potassium phosphide, beryllium phosphide, magnesium phosphide, calcium phosphide, strontium phosphide, barium phosphide, boron phosphide, aluminum phosphide, gallium phosphide, and zinc phosphide, with at least 4 moles of an aldehyde having the formula RCHO, per gram atom of the phosphorus, and from 1 to 10 moles of the said mineral acid, per gram atom of the phosphorus, at a temperature of from $-10°$ C to $100°$ C in the presence of an inert gas atmosphere, and with at least one and a half moles of water being present per gram atom of the phosphorus of the said metal phosphide.

3. A process for preparing tetrakis(hydroxymethyl)-phosphonium chloride, which comprises reacting a metal phosphide selected from the group consisting of lithium phosphide, sodium phosphide, potassium phosphide, beryllium phosphide, magnesium phosphide, calcium phosphide, strontium phosphide, barium phosphide, boron phosphide, aluminum phosphide, gallium phosphide, and zinc phosphide, with at least 4 moles of formaldehyde, per gram atom of the phosphorus, and from 1 to 10 moles of hydrochloric acid, per gram atom of the phosphorus, at a temperature of from $-10°$ C to $100°$ C in the presence of an inert gas atmosphere, and with at least one and a half moles of water being present per gram atom of the phosphorus of the said metal phosphide.

4. A process for preparing the compound $P[CH(OH)R]_4X$ in which R is H or an alkyl group of from 1 to 11 carbon atoms, and X is the anion of a mineral acid, HX, which comprises reacting a metal phosphide selected from the group consisting of magnesium phosphide, calcium phosphide, aluminum phosphide, and zinc phosphide, with at least 4 moles of an aldehyde having the formula RCHO, per gram atom of the phosphorus, and from 1 to 10 moles of the said mineral acid, per gram atom of the phosphorus, at a temperature of from $-10°$ to $100°$ C in the presence of an inert gas atmosphere, and with at least one and a half moles of water being present per gram atom of phosphorus of the said metal phosphide.

5. A process according to claim 1 in which the aldehyde is formaldehyde.

6. A process according to claim 1 in which the aldehyde is acetaldehyde.

7. A process as in claim 1 in which the aldehyde is butyraldehyde.

8. A process as in claim 1 in which the aldehyde is heptaldehyde.

9. A process as in claim 1 in which the aldehyde is phenylacetaldehyde.

* * * * *